United States Patent [19]

Calvin

[11] Patent Number: 5,121,630

[45] Date of Patent: Jun. 16, 1992

[54] MATERIAL MONITORING DEVICE

[76] Inventor: Noel M. Calvin, 4201 Page Mill Rd., Los Altos, Calif. 94023

[21] Appl. No.: 633,031

[22] Filed: Dec. 21, 1990

[51] Int. Cl.5 ............... G01N 27/22; A61B 19/00; G08B 21/00

[52] U.S. Cl. ............... 73/73; 73/304 C; 128/886; 340/573; 340/604

[58] Field of Search ............... 73/73, 74, 304 C; 128/886; 340/573, 601, 602, 604

[56] References Cited

U.S. PATENT DOCUMENTS

| | | | |
|---|---|---|---|
| 2,579,316 | 12/1951 | Hall et al. | 175/183 |
| 2,668,202 | 2/1954 | Kaplan | 200/61.05 |
| 3,171,934 | 3/1965 | Brennan et al. | 200/138 |
| 3,508,235 | 4/1970 | Baisden | 340/235 |
| 3,530,855 | 9/1970 | Balding | 128/138 |
| 3,818,468 | 6/1974 | Toth et al. | 340/224 |
| 3,824,460 | 7/1974 | Gustafson | 324/61 R |
| 3,927,370 | 12/1975 | De Bough | 324/65 R |
| 4,013,065 | 3/1977 | Copeland et al. | 73/73 X |
| 4,069,817 | 1/1978 | Fenole et al. | 128/138 |
| 4,106,001 | 8/1978 | Mahoney | 340/604 |
| 4,163,449 | 8/1979 | Regal | 128/886 |
| 4,197,530 | 4/1980 | Lane | 73/73 X |
| 4,199,984 | 4/1980 | Huddart et al. | 73/304 C |
| 4,205,672 | 6/1980 | Dvorak | 128/138 |
| 4,271,406 | 6/1981 | Wilson | 340/604 |
| 4,653,491 | 3/1987 | Okada et al. | 128/138 |
| 4,800,370 | 1/1989 | Vetecnik | 340/604 |

FOREIGN PATENT DOCUMENTS

| | | | |
|---|---|---|---|
| 203949 | 11/1984 | Japan | 340/604 |
| 167263 | 7/1988 | Japan | 73/73 |
| 2113438 | 8/1983 | United Kingdom | 128/886 |

Primary Examiner—William A. Cuchlinski, Jr.
Assistant Examiner—G. Bradley Bennett
Attorney, Agent, or Firm—Burns, Doane, Swecker & Mathis

[57] ABSTRACT

The present invention is directed to devices for detecting the moisture content of material such as a diaper using a change in bulk dielectric constant. More particularly, the invention relates to a moisture sensing device which provides an accurate indication of the moisture content of a material such as a diaper when merely placed in the vicinity of the diaper. In a preferred embodiment, the device is a hand-held device which can be readily transported and which can detect diaper moisture without piercing the diaper or attaching electrodes directly to the diaper.

11 Claims, 3 Drawing Sheets

MATERIAL MONITORING DEVICE

BACKGROUND OF THE INVENTION

1. Field of the Invention

The present invention relates generally to moisture detection. More particularly, the invention relates to devices for sensing moisture of a material, such as a diaper.

2. State of the Art

In the past, liquid detectors have been devised for determining the presence of moisture in an article of clothing such as an infant's diaper or undergarment. For example, U.S. Pat. No. 3,818,468 discloses a portable detector which includes first and second probes. More particularly, this patent discloses a resistive type detector which is operated by attaching the probes to the article of clothing where moisture is to be detected. When sufficient moisture exists in the layers of the material being sensed, a reduced resistance path is formed between the ends of the probes attached thereto. A signal is transmitted to indicate when the ohmic resistance drops below a pre-determined value.

Further, U.S. Pat. No. 2,579,316 relates to a pressure sensitive moisture testing instrument. This patent discloses a circuit which establishes either a current flow or an electric field through a material for which moisture is to be tested. The current flow or electric field, as the case may be, is influenced by the moisture content present in the material, causing a corresponding change in current flow or voltage in the circuit. Although column 1, lines 16-20 refer to several varieties of this general circuit, one of which includes "the dielectric type" dependent upon change in dielectric constant with variations in moisture, specific circuitry related to this type of device is not disclosed.

U.S. Pat. No. 3,824,460 relates to a capacitive sensing system for detecting the presence of a liquid on a floor or the like using a sensing probe. Two parallel wires are encased in a plastic material spaced by webbed portions made of the same material so as to form a flat cable assembly which may be installed on a floor where leakage is to be detected. Leakage on the floor causes liquid to fill into the spaces between the two wires where the web is not present, thus changing the dielectric constant between the two wires and influencing the overall capacitance of the sensor. This change in dielectric constant results in a change of current through the capacitor and is used to provide an output alarm.

Although devices for detecting moisture are known, a relatively accurate, cost effective moisture detecting device for sensing the moisture content of a material such as a diaper would be desirable.

SUMMARY OF THE INVENTION

The present invention is directed to devices for detecting the moisture content of material such as a diaper using a change in dielectric constant. More particularly, the invention relates to a moisture sensing device which provides a accurate indication of the moisture content of a material when merely placed in the vicinity of the material. In a preferred embodiment, the device is a hand-held device which can be readily transported and which can detect material moisture without piercing the material or attaching electrodes directly to the material.

BRIEF DESCRIPTION OF THE DRAWING

Other objects and advantages of the present invention will become apparent from the following detailed description of preferred embodiments when read in conjunction with the accompanying drawings wherein like elements are assigned like reference numerals, and wherein.

DETAILED DESCRIPTION OF PREFERRED EMBODIMENTS

In the following description of preferred embodiments, specific reference will be made to a moisture detector for sensing moisture present in a material such as a diaper. However it will be readily apparent to those skilled in the art that such a detector can be applied to the detection of any material wherein the sensing of moisture is desired.

The present invention relates to devices for detecting moisture content of a material by detecting changes in the bulk dielectric constant of the material. Using changes in the bulk dielectric constant to determine moisture content permits the detector to be a portable sensing device which need not be directly connected with the material or brought into contact with the material in any way. Rather, the detector need merely be brought into the vicinity of the material to provide a determination that moisture is present therein.

Figure 1:
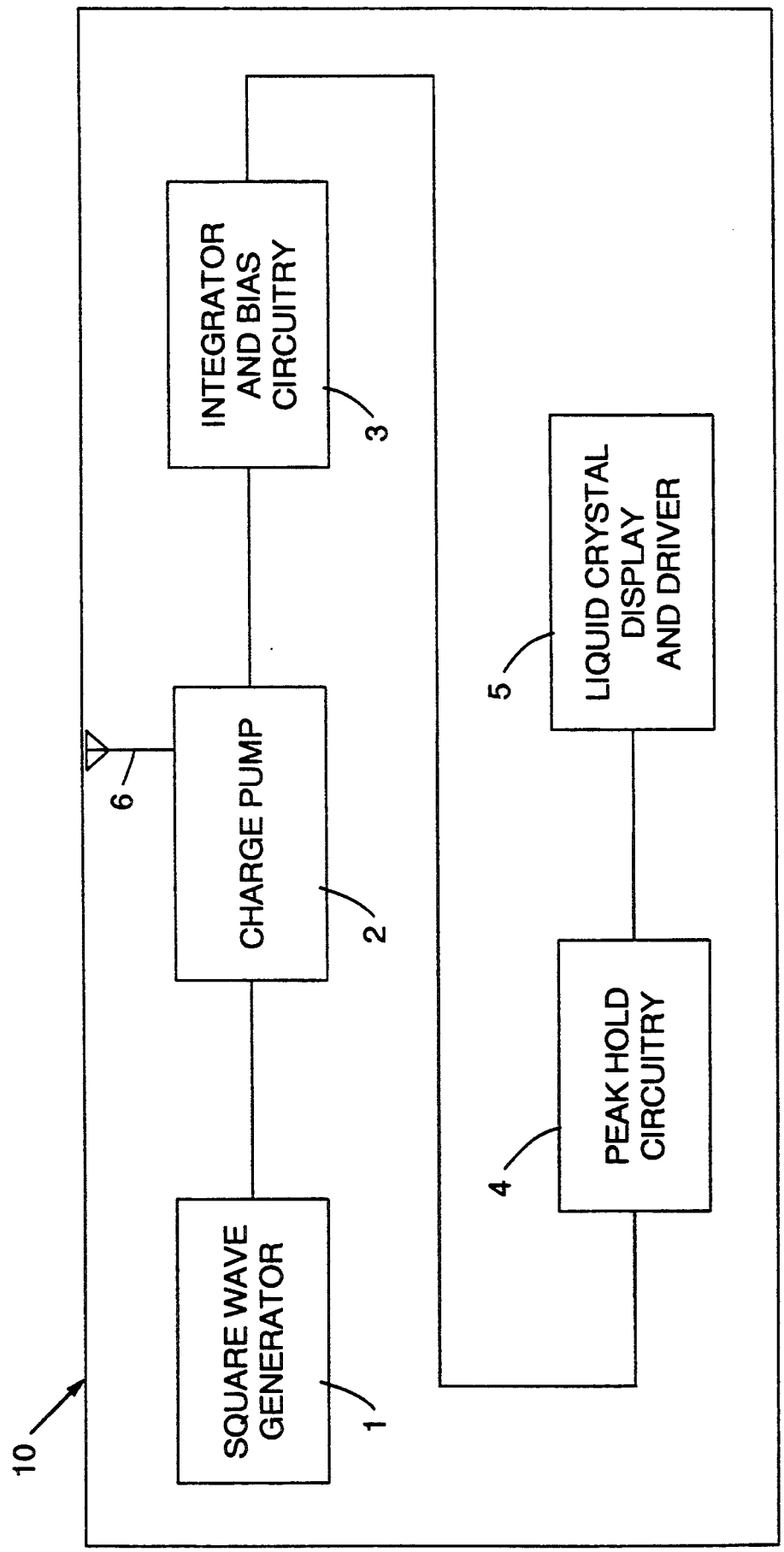
FIG. 1 shows a block diagram of an exemplary preferred embodiment of a device constructed in accordance with the present invention; and, FIGS. 2A-2B show features of the FIG. 1 block diagram in greater detail.

FIG. 1 represents a block diagram of a moisture sensing device 10, such as a capacitance proximity sensing device, which uses changes in the bulk dielectric constant of a material in the vicinity of an antenna to detect moisture content. Generally, the moisture sensing device 10 includes a square wave generator 1, a charge pump 2, an integrator and bias circuitry 3, peak hold circuitry 4 and a liquid crystal display and driver 5. An antenna 6 is the heart of the sensing device, and represents a capacitance proximity sensor. The sensor is composed of a metal plate, the square wave generator, the charge pump and the integrator, the output of which is a current that is proportional to the magnitude of the effective capacitance coupling between the metal plate and a ground plane. The capacitance of the metal plate is affected by the size and relative location of surrounding objects placed in the proximity of the antenna. The sensor thus produces an output which is responsive to changes in the bulk dielectric constant of a material placed in the proximity of the antenna.

The bulk dielectric constant is the property of matter that describes how effective that form of matter is at increasing capacitance. For example, the dielectric constant of air is very low. On the contrary, the dielectric constant of water is quite high. The dielectric constant of dry cloth is typically only slightly higher than that of air. However, the dielectric constant of wet cloth approaches that of water. Thus, when the metal plate of the capacitance proximity sensor is brought close to a wet diaper, the capacitance of the sensor plate will increase much more than it will when the sensor plate is brought close to a dry diaper. Thus, use of this property permits a device such as that shown in FIG. 1 to detect moisture in a cloth when the sensor is brought close to the vicinity of the cloth.

Figure 2A:
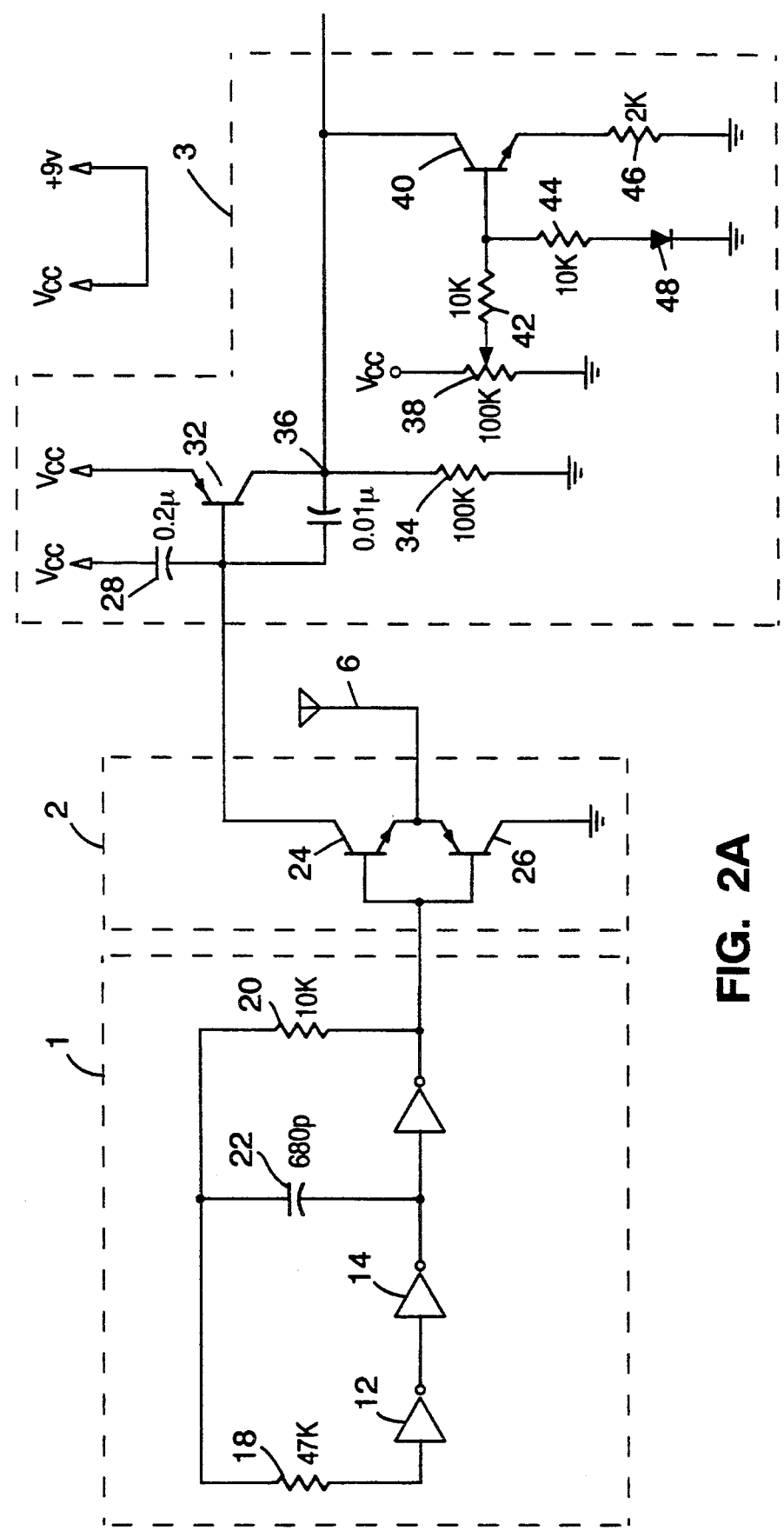
Figure 2B:
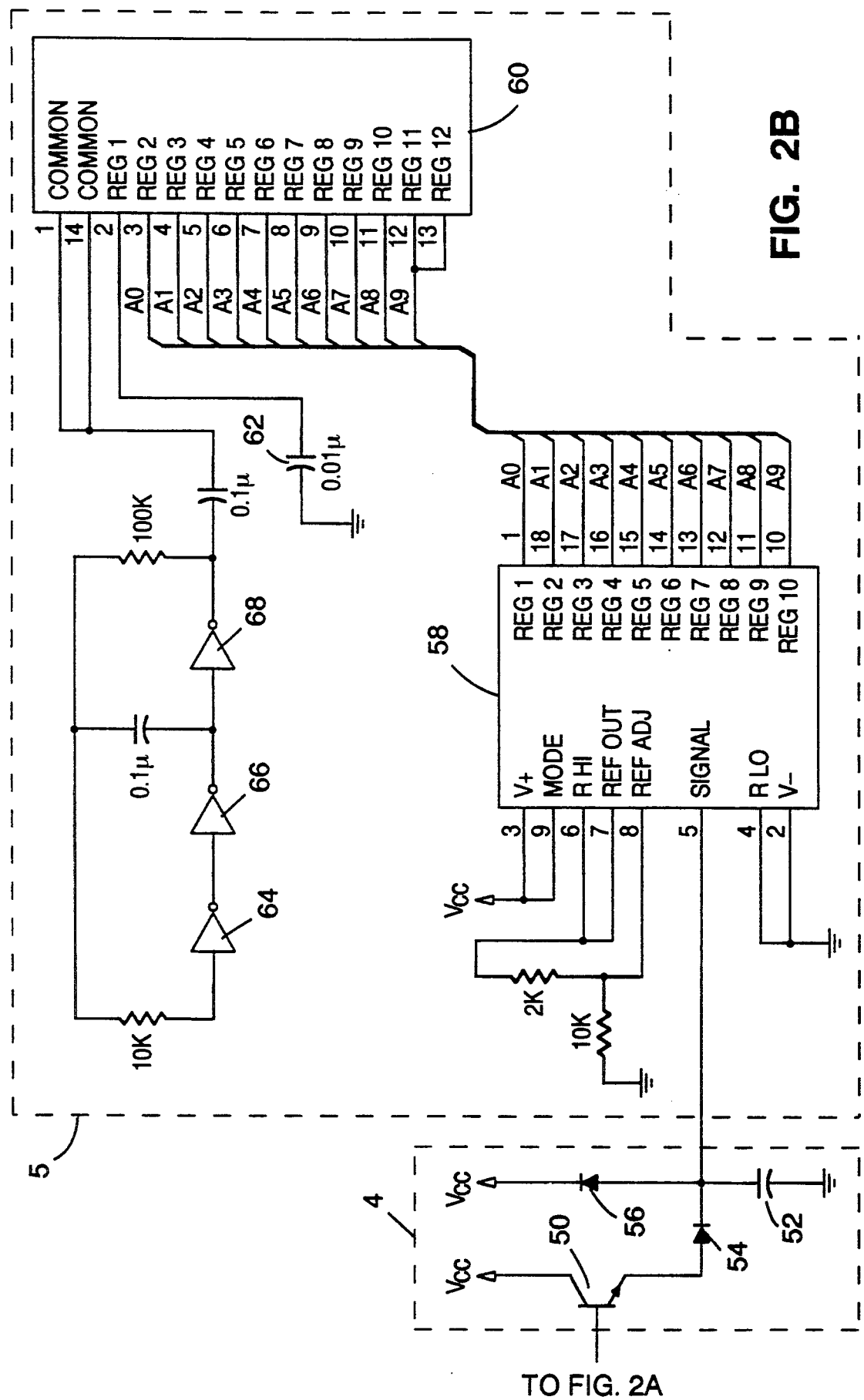

FIGS. 2A–2B show the exemplary moisture sensing device of FIG. 1 in greater detail. More particularly, the square wave generator 1 is shown to include three standard invertors 12, 14, and 16. The input of the first invertor 12 and the output of the third invertor 16 are connected in series via two resistors 18, 20 of 47 kilo-ohms and 10 kilo-ohms, respectively. One plate of a capacitor 22 is connected to a junction between the resistors 18 and 20. The opposite plate of this capacitor 22 is connected to the junction between the output of invertor 14 and the input of invertor 16. The output of invertor 16 represents the output of the square wave generator which is fed to the charge pump 2.

The charge pump 2 includes an n-p-n transistor and a p-n-p transistor configured with their emitters coupled to each other and to the antenna 6. The n-p-n transistor is labelled 24 while the p-n-p transistor is labelled 26. The collector of transistor 26 is connected to ground while that of transistor 24 represents an output of the charge pump 2. Both base inputs of transistors 24 and 26 are connected to the output of the square wave generator 1.

The output of the charge pump is connected to the integrator and bias circuitry 3. More particularly, when moisture is present such that current is conducted via the antenna 6, a capacitor 28 included in the integrator and bias circuitry is charged via a voltage source $V_{cc}$ 30. When the capacitor 28 has been charged sufficiently, a p-n-p transistor 32 is activated such that the voltage $V_{cc}$ is connected to ground via a resistor 34. The voltage drop present across the resistor 34 appears at node 36 and is directed to the output of the integrator and bias circuitry.

A potentiometer 38, a transistor 40, resistors 42, 44 and 46, and a diode 48 are used to provide the bias setting of the moisture sensing device. This bias setting enables the threshold of the sensing device to be adjusted so that the change in moisture of a given material can be detected merely by placing the detector in the vicinity of the material.

The voltage present at node 36 of the integrator and bias circuitry is input to a transistor 50 of peak-hold circuitry 4. During the time that the transistor 50 is activated, a capacitor 52 included in the peak-hold circuitry charges toward the value of $V_{cc}$ via a diode 54. A second diode 56 connected to the non-grounded electrode of the capacitor 52 resets the peak-hold circuitry to zero by permitting the capacitor 52 to quickly discharge when the power is turned off.

The voltage at the capacitor 52 represents the output of the peak-hold circuitry 4, and is input to a liquid crystal display driver 58 of the liquid crystal display and driver 5. In the exemplary embodiment shown in FIGS. 2A–2B, a twelve segment LCD display device 60 is provided. The driver 58 is a ten segment driver. Accordingly, the eleventh and twelfth segments of the LCD display 60 are connected to the tenth segment of the driver 58 while the first segment of the display 60 is connected to ground via a capacitor 62. Display 60 is a well-known LCD display which is connected to a drive source represented by three invertors 64, 66 and 68 in known fashion.

In operation, the known driver 58 responds to the voltage level at the capacitor 52 to provide outputs to one or more of the segment drive lines shown at the output of driver 58. Depending on the number of active segment drive lines provided by the driver 58, a corresponding number of segments in the LCD display 60 will be illuminated. Because the signal at the capacitor 52 is proportional to the bulk dielectric constant of a material placed in the proximity of antenna 6, the display will represent the moisture content of the material.

It will be appreciated by those skilled in the art that FIGS. 1, 2A and 2B merely represent one exemplary embodiment by which the present invention can be implemented. For example, the capacitance sensed by the antenna 6 may be displayed in any number of ways. More particularly, the voltage at the capacitor 52 in the peak-hold circuitry can be connected to a voltage or current controlled oscillator. The voltage controlled oscillator can then be connected to a speaker or piezoelectric transducer such that a user of the moisture sensing device would hear a tone with a pitch proportional to the wetness of the diaper.

Alternately, in place of a liquid crystal display 60 as shown in FIG. 2B, the output voltage at the capacitor 52 can be displayed using a multi-colored LED such that the color of the display indicates the degree of moisture content in a material placed near the antenna 6. For example, green could be used to indicate a dry condition, yellow a damp condition and red a wet condition.

Further, the voltage output at capacitor 52 can be fed to a pulse generator which drives a light or tone generator. In such a case, the repetition rate of flashes of light or beeps can be made proportional to the degree of wetness.

It will be appreciated by those skilled in the art that the present invention can be embodied in other specific forms without departing from the spirit or essential characteristics thereof. The presently disclosed embodiments are therefore considered in all respects to be illustrative and not restrictive. The scope of the invention is indicated by the appended claims rather than the foregoing description, and all changes that come within the meaning and range of equivalence thereof are intended to be embraced therein.

What is claimed is:

1. A moisture sensing device for detecting moisture content of a material comprising:
   a capacitance proximity sensor; and,
   an indicator responsive to an output of said capacitance proximity sensor, said capacitance proximity sensor further including:
   a charge pump; and,
   an antenna formed as a single metal plate for detecting changes in the bulk dielectric constant of a material placed between said metal plate and a variable ground plane.

2. Device according to claim 1, wherein said device is a portable, hand-held device.

3. Device according to claim 1, wherein said capacitance proximity sensor further includes:
   a square wave generator for providing an input to said charge pump;
   an integrator and bias circuit for receiving an output from said charge pump and antenna; and,
   a peak-hold circuit for storing a maximum signal proportional to the bulk dielectric constant of a material.

4. Device according to claim 1, wherein said indicator is a liquid crystal display.

5. Device according to claim 1, wherein said indicator is a multi-colored LED display.

6. Device according to claim 1, wherein said indicator is a light generator which flashes at a rate proportional to the degree of moisture sensed.

7. Device according to claim 1, wherein said indicator is a tone generator having a tone which is adjusted in proportion to the degree of moisture detected b said sensing device.

8. A portable, hand-held moisture sensing device for detecting moisture content of a material comprising:
   a capacitance proximity sensor; and,
   a liquid crystal display indicator responsive to an output of said capacitance proximity sensor, said capacitance proximity sensor further including:
   a charge pump;
   an antenna formed as a single metal plate for detecting changes in the bulk dielectric constant between said metal plate and a variable ground plane;
   a square wave generator for providing an input to said charge pump;
   an integrator and bias circuit for receiving an output from said charge pump and antenna; and,
   a peak-hold circuit for storing a maximum signal proportional to the bulk dielectric constant of a material.

9. Device according to claim 8, wherein said antenna is a first electrode of a capacitor for storing a voltage relative to an earth ground plane.

10. Device according to claim 1, wherein said antenna is a first electrode of a capacitor for storing a voltage relative to an earth ground plane.

11. Device according to claim 3, wherein said square wave generator produces a square wave to measure change accumulated on said metal plate.

* * * * *

UNITED STATES PATENT AND TRADEMARK OFFICE
CERTIFICATE OF CORRECTION

PATENT NO. : 5,121,630

DATED : June 16, 1992

INVENTOR(S) : Noel M. Calvin

It is certified that error appears in the above-identified patent and that said Letters Patent is hereby corrected as shown below:

Column 1, line 62, delete "a" and insert --an-- therefor;

Column 4, line 6, following "FIGS 1", delete "." and insert --,-- therefor;

Column 5, line 6, delete "b" and insert --by-- therefor.

Signed and Sealed this

Seventh Day of September, 1993

*Attest:*

BRUCE LEHMAN

*Attesting Officer*  *Commissioner of Patents and Trademarks*